US006140086A

United States Patent [19]
Fox et al.

[11] Patent Number: 6,140,086
[45] Date of Patent: Oct. 31, 2000

[54] METHODS AND COMPOSITIONS FOR CLONING NUCLEIC ACID MOLECULES

[76] Inventors: Donna K. Fox, 7407 Village Rd., #25, Sykesville, Md. 21784; Deb K. Chatterjee, 6 Forest Ridege Ct., North Potomac, Md. 20878

[21] Appl. No.: 09/134,672

[22] Filed: Aug. 14, 1998

Related U.S. Application Data

[60] Provisional application No. 60/055,849, Aug. 15, 1997.

[51] Int. Cl.$^7$ ........................... C12N 15/64; C12N 15/74; C12N 9/99; C12N 9/12; C12P 19/34
[52] U.S. Cl. .................. 435/91.41; 435/91.1; 435/91.2; 435/91.5; 435/91.52; 435/184; 435/194; 435/471
[58] Field of Search .................................. 435/91.1, 91.2, 435/91.41, 91.5, 91.52, 184, 194, 471

[56] References Cited

U.S. PATENT DOCUMENTS

| | | | |
|---|---|---|---|
| 5,338,671 | 8/1994 | Scalice et al. | 435/91.2 |
| 5,436,149 | 7/1995 | Barnes | 435/194 |
| 5,512,462 | 4/1996 | Cheng | 435/91.2 |
| 5,587,287 | 12/1996 | Scalice et al. | 435/6 |
| 5,814,502 | 9/1998 | Hoeltke et al. | 435/188 |

FOREIGN PATENT DOCUMENTS

| | | |
|---|---|---|
| WO 92/06188 A2 | 4/1992 | WIPO . |
| WO 92/06200 A1 | 4/1992 | WIPO . |
| WO 96/10640 A1 | 4/1996 | WIPO . |
| WO 97/24455 | 7/1997 | WIPO . |

OTHER PUBLICATIONS

Boehringer Mannheim Reagents for Molecular Biology catalog, 1990, pp. 15, 23, 1990.
Buchman, G.W. et al., "Rapid and Efficient Cloning of PCR Products Using the CloneAmp™System," *Focus* 14:41–45 (1992).
Kaufman, D.L. and G.A. Evans, "Restriction Endonuclease Cleavage at the Termini of PCR Products," *BioTechniques* 9:304, 306 (19900.
Mead, D.A. et al., "A Universal Method for the Direct Cloning of PCR Amplified Nucleic Acid," *Bio/Technology* 9:657–663 (1991).
Polayes, D. and A.J. Hughes, Jr., "Efficient Protein Expression and Simple Purification Using the pProEX–1™System," *Focus* 16:81–84 (1994).
Scharf, S.J., "Cloning with PCR, " in PCR Protocols: A Guide to Methods and Applications, New York: Academic Press, Inc., pp. 84–91 (1990).
Wybranietz, W.A. and U. Lauer, "Distinct Combination of Purification Methods Dramatically Improves Cohesive–End Subcloning of PCR Products," *BioTechniques* 24:578–580 (Apr. 1998).
Barnes, W.M., "The fidelity of Taq polymerase catalyzing PCR is improved by an N–terminal deletion," *Gene* 112:29–35 (1992).

Dang, C., and Jayasena, S.D., "Oligonucleotide Inhibitors of Taq DNA Polymerase Facilitate Detection of Low Copy Number Targets by PCR," *J. Mol. Biol.* 264:268–278 (1996).
Flaman, J.—M., et al., "A rapid PCR fidelity assay," *Nucl. Acids Res.* 22:3259–3260 (1994).
Kainz, P., et al., "Specificity–Enhanced Hot–Start PCR: Addition of Double–Stranded DNA Fragments Adapted to the Annealing Temperature," *BioTechniques* 28:278–282 (2000).
Kellogg, D.E., et al., TaqStart Antibody™: "Hot Start" PCR Facilitated by a Neutralizing Monoclonal Antibody Directed Against Taq DNA Polymerase, *BioTechniques* 16:1134–1137 (1994).
Lawyer, F.C., et al., "High–level Expression, Purification, and Enzymatic Characterization of Full–Length *Thermus aquaticus* DNA Polymerase and a Truncated Form Deficient in 5'to 3'Exonuclease Activity," *PCR Meth. Appl.* 2:275–287 (1993).
Lin, Y., and Jayasena, S.D., "Inhibition of Multiple Thermostable DNA Polymerases by a Heterodimeric Aptamer," *J. Mol. Biol.* 271:100–111 (Aug. 1997).
New England Biolabs, Beverly, MA, product information for VENT®, DEEPVENT™, and other thermophilic DNA polymerases, NEB 1996–1997 Products Catalogue, pp. 70–71 (1996).
Newton, C.R., "Thermostable DNA Polymerases," in: *PCR Essential Data*, C.R. Newton, Ed., New York: John Wiley & Sons, pp. 37–48 (1995).
Kahl, G., "Dictionary of Gene Technology," New York: VCH Publishers, Inc., pp. 140, 411, 510 (1995).
Life Technologies, Inc., "GIBCO BRL Products and Reference Guide 1997/1998," pp. 19–18 to 19–19 (1997).
Gerald, G.F., "Reverse Transcriptase: A Historical Perspective," *Focus* 20(3):65–67 (Fall 1998).
Bennett, B.L., and Molenaar, A.J., "Cloning of PCR Products Can be Inhibited by Taq Polymerase Carryover," *BioTechniques* 16:32,37 (Jan. 1994).

(List continued on next page.)

*Primary Examiner*—Carla J. Myers
*Assistant Examiner*—Diana Johannsen
*Attorney, Agent, or Firm*—Sterne, Kessler, Goldstein & Fox P.L.L.C.

[57] ABSTRACT

The present invention is directed generally to methods facilitating the cloning of nucleic acid molecules. In particular, the invention relates to the use of polymerase inhibitors, including but not limited to anti-polymerase antibodies (such as anti-Taq antibodies) and fragments thereof, to inactivate residual polymerase activity remaining after the amplification (particularly via PCR) of a target nucleic acid molecule. The invention further provides compositions, particularly storage-stable compositions, comprising one or more components, such as one or more restriction endonucleases and one or more polymerase inhibitors, that are useful in cloning amplified or synthesized nucleic acid molecules by the above-described methods. The invention also relates to nucleic acid molecules produced by these methods, and to genetic constructs (such as vectors) and host cells comprising these nucleic acid molecules.

27 Claims, 1 Drawing Sheet

OTHER PUBLICATIONS

Fox, D., et al., "Prevention of Taq DNA Polymerase–Mediated Artifacts in PCR Product Cloning," *Focus* 20:15–16 (Mar. 1998).

Innis, M.A., et al., "DNA sequencing with *Thermus aquaticus* DNA polymerase and direct sequencing of polymerase chain reaction–amplified DNA," *Proc. Natl. Acad. Sci. USA* 85:9436–9440 (Dec. 1988).

Nilsson, J., et al., "Heat–Mediated Activation of Affinity–Immobilized Taq DNA Polymerase," *BioTechniques* 22:744–751 (Apr. 1997).

METHODS AND COMPOSITIONS FOR CLONING NUCLEIC ACID MOLECULES

CROSS REFERENCE TO RELATED APPLICATION

This application claims the benefit of U.S. Provisional Application No. 60/055,849, filed Aug. 15, 1997, the disclosure of which is entirely incorporated herein by reference.

BACKGROUND OF THE INVENTION

1. Field of the Invention

This invention is in the fields of molecular and cellular biology. The invention is generally directed to amplification of nucleic acid molecules and to methods for cloning nucleic acid molecules (DNA or RNA) that have been amplified or synthesized, particularly those nucleic acid molecules that have undergone PCR amplification. In particular, the invention concerns methods of cloning amplified nucleic acid molecules comprising the use of inhibitors of nucleic acid polymerases that carry out the amplification. The invention further concerns nucleic acid molecules produced by such methods and vectors and host cells comprising such nucleic acid molecules. The invention further relates to compositions for facilitating cloning of amplified nucleic acid molecules.

2. Related Art

Cloning of Nucleic Acid Molecules

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist myriad mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A binds to T, the mRNA molecules can be rapidly purified from other molecules and substances in the tissue or cell extract. From these purified mRNA molecules, cDNA copies may be made using one or more polypeptides having reverse transcriptase (RT) activity, which results in the production of single-stranded cDNA molecules. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a polypeptide having nucleic acid polymerase activity, such as a DNA polymerase. The protein-specific double-stranded cDNAs can then be inserted into a plasmid or viral vector (also called cloning vehicles), using controlled restriction enzyme digestion and ligation of the cDNA and the vehicle. The resulting cDNA-vehicle construct is then introduced into a bacterial host, yeast, animal or plant cell and the host cells are then grown in culture media, resulting in a population of host cells containing (or in some cases, expressing) the gene of interest.

This entire process, from isolation of mRNA to insertion of the cDNA into a plasmid or vector to growth of host cell populations containing the isolated gene, is termed "cDNA cloning." If cDNAs are prepared from a number of different mRNAs, the resulting set of cDNAs is called a "cDNA library" which represents a population of genes comprising the functional genetic information present in the source cell, tissue or organism.

A variety of procedures are useful to clone genes. One such method entails analyzing a library of cDNA inserts (derived from a cell expressing the corresponding protein) for the presence of an insert which contains the desired gene. Such an analysis may be conducted by transfecting cells with the vector, inducing the expression of the protein, and then assaying for protein expression, for example, by immunoreaction with an antibody which is specific for the desired protein.

Alternatively, in order to detect the presence of the desired gene, one may employ an oligonucleotide (or set of oligonucleotides) which have a nucleotide sequence that is complementary to the oligonucleotide sequence or set of sequences that codes for the desired protein. Such oligonucleotides are used to detect and/or isolate the desired gene by selective hybridization. Techniques of nucleic acid hybridization are disclosed by Maniatis, T., et al., In: *Molecular Cloning, a Laboratory Manual*, Cold Spring Harbor, N.Y. (1982), and by Haymes, B. D., et al., In: *Nucleic Acid Hybridization, a Practical Approach*, IRL Press, Washington, D.C. (1985), which references are herein incorporated by reference.

In addition to the above methods, most commonly used cloning vectors have an indicator gene which results in the expression of a specific phenotype in host cells containing the vector (e.g., blue colonies for host cells containing vectors that carry lacZα; see Maniatis, T., et al., Id.). Insertion of heterologous nucleic acid sequences into multiple cloning sites in such vectors interrupts or inactivates the indicator gene, resulting in non-expression of the phenotype (e.g., white colonies for the above-described host cells containing lacZα vectors). Such an approach provides a convenient means for differentiating recombinant clones (i.e., those forming white colonies) from non-recombinant clones (i.e., those forming blue colonies). However, this approach does not prevent the growth of non-recombinant clones.

Nucleic Acid Amplification

Soon after their identification and characterization, it was recognized that the activities of the various enzymes and cofactors involved in nucleic acid synthesis could be exploited in vitro to dramatically increase the concentration of, or "amplify," one or more selected nucleotide sequences. For many medical, diagnostic and forensic applications, amplification of a particular nucleic acid molecule is essential to allow its detection in, or isolation from, a sample in which it is present in very low amounts. More recently, in vitro amplification of specific genes has provided powerful and less costly means to facilitate the production of therapeutic proteins by molecular biological techniques, and may have applications in genetic therapy as well.

While a variety of nucleic acid amplification processes have been described, the most commonly employed is the Polymerase Chain Reaction (PCR) technique disclosed in U.S. Pat. Nos. 4,683,195 and 4,683,202. In this process, a sample containing the nucleic acid sequence to be amplified (the "target sequence") is first heated to denature or separate the two strands of the nucleic acid. The sample is then cooled and mixed with specific oligonucleotide primers which hybridize to the target sequence. Following this hybridization, a buffered aqueous solution containing at least one polypeptide having DNA polymerase activity is added to the sample, along with a mixture of the dNTPs that are linked by the polymerase to the replicating nucleic acid strand. After allowing polymerization to proceed to completion, the products are again heat-denatured, subjected to another round of primer hybridization and polymerase replication, and this process is repeated any number of times. Since each nucleic acid product of a given cycle of this process serves as a template for production of two new nucleic acid molecules (one from each parent strand), the PCR process results in an exponential increase in the concentration of the target sequence. Thus, in a well-controlled, high-fidelity PCR process, as few as 20 cycles can result in an over one million-fold amplification of the target nucleic acid sequence (See U.S. Pat. Nos. 4,683,195 and 4,683,202).

Other techniques for amplification of target nucleic acid sequences have also been developed. For example, Walker et al. (U.S. Pat. No. 5,455,166; EP 0 684 315) described a method called Strand Displacement Amplification (SDA), which differs from PCR in that it operates at a single temperature and uses a polymerase/endonuclease combination of enzymes to generate single-stranded fragments of the target DNA sequence, which then serve as templates for the production of complementary DNA (cDNA) strands. An alternative amplification procedure, termed Nucleic Acid Sequence-Based Amplification (NASBA) was disclosed by Davey et al. (U.S. Pat. No. 5,409,818; EP 0 329 822). Similar to SDA, NASBA employs an isothermal reaction, but is based on the use of RNA primers for amplification rather than DNA primers as in PCR or SDA.

Amplification-Based Cloning

Standard cloning techniques such as those described above are often useful for cloning nucleic acid sequences that are expressed at relatively high levels in the source cells or tissues. However, these techniques frequently are not particularly sensitive when the starting samples contain only low levels of the nucleic acid molecule of interest. This problem is particularly important when the tissue or cell samples are themselves present in low quantities (as in many medical or forensic applications), or when the specific nucleotide sequence is present or expressed at low levels in the cell/tissue samples.

Amplification-based cloning of nucleic acid molecules, particularly that employing PCR, has been used in the attempt to overcome the lack of sensitivity of earlier approaches (see, e.g., Lee, C. C., et al., *Science* 239:1288–1291 (1988)). There are a number of methods available for performing such cloning.

In one such method, restriction enzyme sites can be incorporated into the PCR primers; the PCR-generated nucleic acid molecules will thus contain these restriction sites. For cloning of these specific sequences, these amplified nucleic acid molecules can then be digested with restriction enzymes, the digested fragments ligated into an appropriate site within a plasmid vector, and the vector incorporated into a host cell.

Alternatively, PCR products generated by Taq DNA polymerase, which typically contain an additional deoxyadenosine (dA) residue at their 3' termini, can be cloned into specific cloning vectors containing 3' deoxythymidine (dT) overhangs which provide a specific recognition sequence for the 3' A residue on the PCR product. This process, often referred to as "TA cloning," provides a means of directly cloning PCR-amplified nucleic acid molecules without the need for preparation of primers with specific restriction sites (see U.S. Pat. No. 5,487,993, which is incorporated herein by reference in its entirety).

In other cloning methods, blunt-end PCR fragments generated by cleavage with certain restriction enzymes (e.g., SmaI, SspI or ScaI) can be cloned into blunt-end insertion sites of cloning vectors (see, e.g., Ausubel, F. M., et al., eds., "Current Protocols in Molecular Biology," New York: John Wiley & Sons, Inc., pp. 3.16.1–3.16.11 (1995)), or PCR-amplified nucleic acid molecules can be cloned using uracil DNA glycosylase (UDG, see U.S. Pat. No. 5,137,814, which is incorporated herein by reference in its entirety). Such blunt-end cloning may also be facilitated by treatment of Taq-amplified PCR products, which contain dA overhangs as described above, with T4 DNA polymerase to remove the dA overhangs (a procedure often termed "polishing") followed by insertion of the resulting blunt-end fragments into blunt-end vector insertion sites as generally described above.

However, the cloning of amplified nucleic acid molecules, especially by restriction enzyme digestion and insertion into cloning vehicles, is usually not simple and straightforward. Problems that plague the investigator are low cloning efficiencies (i.e., a low number of recombinant clones obtained per transformation) and cloning artifacts (i.e., recombinant clones which contain a modified insert). The probable cause of such technical limitations is residual polymerase activity which remains in the reaction mixture after the amplification process (see Bennet, B. L., and Molenaar, A. J., *BioTechniques* 16:36–37 (1994)). In fact, it has been shown that after 30 rounds of amplification under standard PCR conditions, sufficient residual polymerase activity is present in the reaction mixture to conduct an additional 30 rounds of amplification. Upon digestion of the termini of the amplified nucleic acid molecules with restriction endonucleases to generate 3' recessed ("sticky") ends in the initial stages of cloning, this residual polymerase can utilize remaining dNTPs in the sample to fill in the 3' ends to regenerate an undesirable blunt end. This interference results in poor ligation of the digested insert into a prepared recipient cloning vector which has been manipulated to possess recessed ends compatible with those of the insert. In fact, even the addition of a single nucleotide to the 3' sticky end can inhibit the ligation process and increase the number of incorrect recombinants that an operator must screen. An additional complication is that if the insert is to be ligated into an expression vector for transformation into a host cell to ultimately generate a protein encoded by the insert, the addition of nucleotides to the digested amplification products can often shift the reading frame of the insert and result in expression of an incomplete, mutant and/or nonfunctional protein, especially if the promoter resides in the cloning vector 5' to the insert.

One often-used approach to attempting to solve this technical problem involves multiple organic phenol/ chloroform extractions of the amplified nucleic acid molecules, prior to cloning, to aid in the removal of the residual polymerases. Analogous methods involve similar time-consuming technical manipulations such as successive rounds of ethanol precipitation and agarose gel purification. While such techniques may reduce the content of the amplifying polymerase to some extent, they also usually result in reduced yields of clonable product due to loss, destruction and/or structural alteration of the amplified nucleic acid molecules during purification. Thus, the temporal and economic constraints to efficient and high-yield cloning of amplified nucleic acid molecules have yet to be overcome.

BRIEF SUMMARY OF THE INVENTION

The present invention relates generally to methods that overcome these temporal and economic constraints, providing for high-efficiency and rapid cloning of nucleic acid molecules, in particular amplified nucleic acid molecules. Specifically, the methods of the invention entail the use of one or more inhibitors of polymerases in the cloning procedure, whereby residual polymerase activity remaining in the reaction mixture after nucleic acid synthesis or amplification is inactivated or inhibited, such that the nucleic acid molecules may be efficiently ligated into a cloning vector.

In one embodiment, the cloning methods of the invention comprise (a) amplifying or synthesizing one more nucleic acid molecules in the presence of one of more polypeptides having polymerase activity to produce copies of the nucleic acid molecules; and (b) incubating the amplified or synthesized nucleic acid molecules with one or more inhibitors of the polypeptides having polymerase activity under conditions sufficient to inhibit or inactivate the polymerase activity. These methods of the invention may further comprise digesting the amplified or synthesized nucleic acid molecules with one or more restriction endonucleases, to produce digested nucleic acid molecules, ligating the amplified, synthesized or digested nucleic acid molecules into one or more vectors to form one or more genetic constructs, and transforming the genetic constructs into one or more host cells. Preferably, the inhibition or inactivation of the polypeptides having polymerase activity increases the efficiency of cloning of the amplified, synthesized or digested nucleic acid molecules into one or more vectors. In addition, the inhibitors used in these methods preferably prevent or inhibit modification of one or more termini of the amplified or digested nucleic acid molecules, and allow increased efficiency of cloning of the amplified, synthesized or digested nucleic acid molecules into one or more vectors.

The invention also relates to nucleic acid molecules produced by the above-described methods.

According to the invention, the amplification step of the above-described methods may comprise:

(a) contacting a first nucleic acid molecule, a first primer nucleic acid molecule which is complementary to a portion of the first nucleic acid molecule, a second nucleic acid molecule and a second primer nucleic acid molecule which is complementary to a portion of the second nucleic acid molecule, with one or more polypeptides having polymerase activity;

(b) incubating the molecules under conditions sufficient to form a third nucleic acid molecule complementary to all or a portion of the first nucleic acid molecule and a fourth nucleic acid molecule complementary to all or a portion of the second nucleic acid molecule;

(c) denaturing the first and third and the second and fourth nucleic acid molecules; and (d) repeating steps (a) through (c) one or more times.

In another aspect, the invention relates to such methods wherein the first and/or second primer nucleic acid molecules comprise one or more recombination sites (recombinase recognition sites) or portions thereof. Nucleic acid molecules synthesized according to this aspect of the invention thus will comprise one or more recombination sites or portions thereof, thereby facilitating easy movement or exchange of nucleic acid segments between different synthesized nucleic acid molecules using one or more recombinase proteins, as described below.

In accordance with the invention, the nucleic acid synthesis step in the above methods may comprise:

(a) mixing a nucleic acid template (e.g., and RNA or a DNA molecule, preferably an mRNA molecule) with one or more polypeptides having polymerase activity; and (b) incubating the mixture under conditions sufficient to make a nucleic acid molecule complementary to all or a portion of the template.

In preferred such aspects, the one or more DNA molecules synthesized by the above methods may be one or more double-stranded cDNA molecules.

The polypeptides having polymerase activity that are preferred for use in these methods of the invention may be DNA polymerases (including thermostable DNA polymerases) or reverse transcriptases. Preferred DNA polymerases include Taq DNA polymerase, tne DNA polymerase, Tma DNA polymerase, Pfu DNA polymerase, Tfl DNA polymerase, Tth DNA polymerase, Pwo DNA polymerase, Bst DNA polymerase, Bca DNA polymerase, VENT®Tli DNA polymerase, DEEPVENT™ Pyrococcus species GB-D DNA polymerase, T7 DNA polymerase, DNA polymerase III, Klenow fragment DNA polymerase, Stoffel fragment DNA polymerase, and mutants, fragments or derivatives thereof. Preferred reverse transcriptases include M-MLV reverse transcriptase, RSV reverse transcriptase, AMV reverse transcriptase, RAV reverse transcriptase, MAV reverse transcriptase, HIV reverse transcriptase, M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase, and mutants, fragments or derivatives thereof.

Preferred polymerase inhibitors for use in the methods of the present invention include, but are not limited to, antibodies (particularly anti-Taq, anti-Tne, anti-Pfu or anti-Tma antibodies) or fragments thereof, chemical compounds, antibiotics, heavy metals, acids, metal chelators, nucleotide analogues, sulfhydryl reagents, anionic detergents, polyanions, captan ((N-[trichloromethyl]-thio)-4-cyclohexene-1,2-dicarboximide), acidic polysaccharides, and combinations thereof In another aspect, the invention relates to methods of ligating an amplified, synthesized or digested nucleic acid molecule into a vector with increased efficiency, comprising:

(a) forming a mixture comprising the nucleic acid molecule and one or more polymerase inhibitors; and (b) ligating the nucleic acid molecule into one or more vectors to form one or more genetic constructs.

The mixtures used in these methods may optionally further comprise one or more polypeptides having polymerase activity. In addition, these methods of the invention may further comprise transforming the one or more genetic constructs into one or more host cells.

The invention also relates to methods for cloning one or more nucleic acid molecules into one or more vectors, comprising:

(a) forming a mixture comprising the nucleic acid molecules to be cloned (which may be amplified, synthesized or digested nucleic acid molecules), the vectors and one or more polymerase inhibitors; and (b) ligating the nucleic acid molecules into the vectors to form one or more genetic constructs.

In another embodiment, the invention relates to such cloning methods wherein the one or more nucleic acid molecules and/or one or more vectors may comprise one or more engineered recombination sites.

In preferred such methods, the nucleic acid molecules are cDNA molecules.

These methods of the invention may further comprise transforming the one or more genetic constructs into one or more host cells.

In another embodiment, the invention relates to methods for cloning one or more nucleic acid molecules into one or more vectors, comprising:

(a) forming a mixture comprising the nucleic acid molecules to be cloned (which may be synthesized or amplified nucleic acid molecules), one or more polymerase inhibitors and one or more restriction endonucleases; and (b) ligating the nucleic acid molecules into one or more vectors to form one or more genetic constructs.

In another embodiment, the invention relates to such cloning methods wherein the one or more nucleic acid molecules and/or one or more vectors may comprise one or more engineered recombination sites.

The mixtures used in these methods may optionally further comprise one or more polypeptides having polymerase activity. In addition, these methods of the invention may further comprise transforming the one or more genetic constructs into one or more host cells. In one preferred such method, the polymerase inhibitors and the restriction endonucleases may be added simultaneously. In another preferred method, the polymerase inhibitors and the restriction endonucleases may be added sequentially.

Methods of the invention may involve any standard cloning methods in which a nucleic acid molecule is inserted into a vector. In particular, the invention concerns the use of topoisomerase, which can cleave a vector to produce 3' dT overhangs and ligate an amplified fragment which contains 3' dA overhangs (produced, for example, by Taq DNA polymerase). Other enzymes for cleaving and ligating (e.g., DNA-modifying enzymes), used in cloning nucleic acid molecules into vectors, may also be used in accordance with the invention. In the above-described methods wherein the amplification primers and/or cloned nucleic acid molecules contain one or more engineered recombination sites, for example, one or more recombination proteins may be used in the above-noted standard cloning methods. Recombination proteins which may be used in accordance with this aspect of the invention include but are not limited to site-specific recombinases, such as (a) the integrase family of recombinases (Argos et al. *EMBO J.* 5:433–440 (1986)) including bacteriophage λ integrase, (Landy, A. (1993) *Current Opinions in Genetics and Devel.* 3:699–707), Cre from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109), and FLP from *Saccharomyces cerevisiae* (Broach et al., *Cell* 29:227–234 (1982)); and (b) the resolvase family of recombinases (e.g., γδ, Tn3 resolvase, Hin, Gin, and Cin) (Maeser and Kahnmann (1991) *Mol. Gen. Genet.* 230:170–176). Other site-specific recombinases may also be used in accordance with the methods of the invention, including the site-specific recombination proteins encoded by bacteriophage lambda, phi 80, P22, P2, 186, P4 and P1 which are known in the art.

In another aspect, the invention also relates to kits for cloning an amplified, synthesized or digested nucleic acid molecule. Kits according to the invention may comprise one or more containers containing one or more of the above-described polymerase inhibitors. Such kits may further comprise one or more additional containers containing, for example, one or more polypeptides having polymerase activity, one or more primer nucleic acid molecules, one or more nucleotides, one or more polypeptides having reverse transcriptase activity, one or more ligases, one or more vectors, one or more host cells (which may be competent for transformation), one or more topoisomerases and one or more restriction endonucleases.

The invention also relates to compositions comprising one or more restriction endonucleases and one or more of the above-described polymerase inhibitors, either or both of which may be stable upon storage. Compositions of the invention also comprise the above-described polymerase inhibitors and one or more DNA modifying enzymes or combinations thereof (such as ligases, kinases, phosphatases, nucleases, endonucleases, topoisomerases, gyrases, terminal deoxynucleotidyl transferases, etc.) Compositions according to this aspect of the invention may further comprise one or more additional components, including, for example, one or more nucleic acid molecules or one or more suitable buffers.

Other preferred embodiments of the present invention will be apparent to one of ordinary skill in light of the following drawings and description of the invention, and of the claims.

DETAILED DESCRIPTION OF THE INVENTION

Definitions

Figure 1:
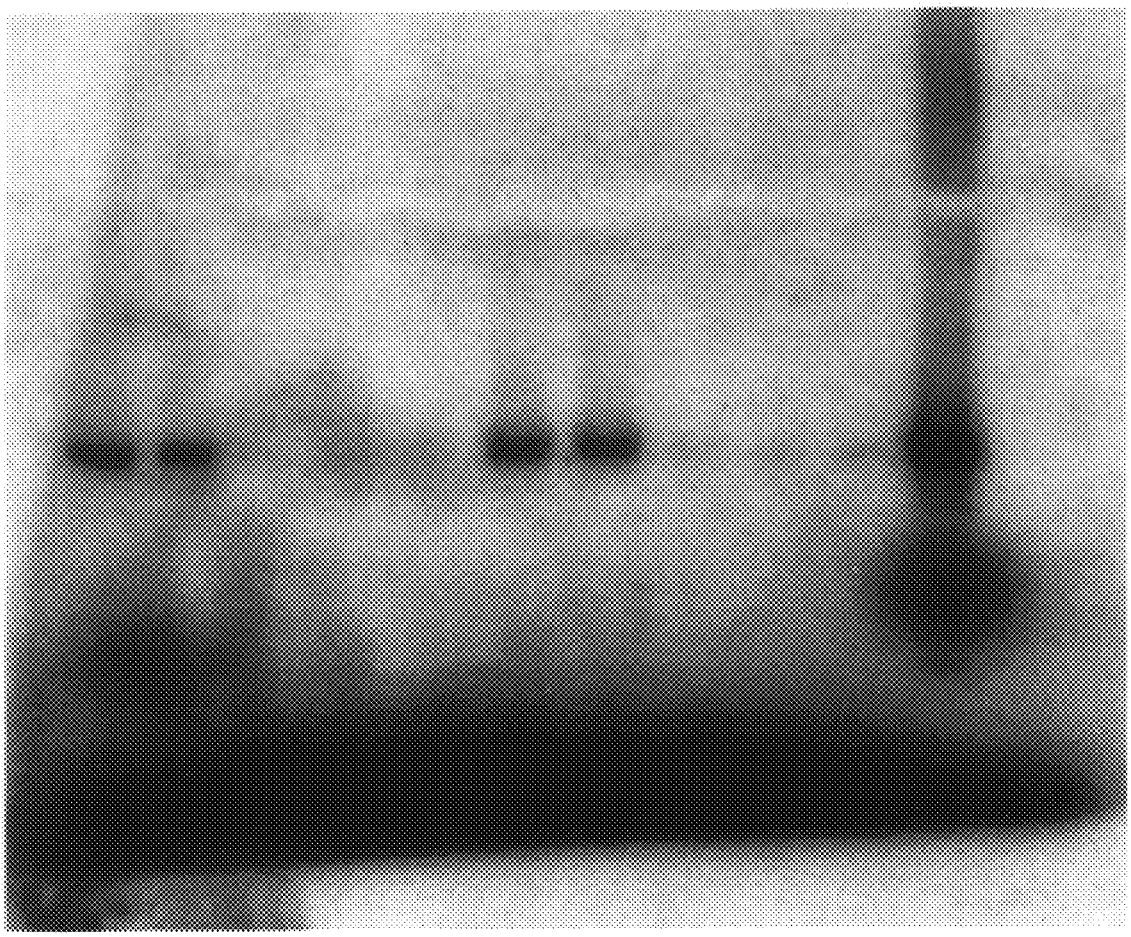
FIG. 1 is an autoradiograph of a 552 bp amplification product obtained by Taq polymerase-mediated amplification of a 664 bp amplification of the 3' end of the chloramphenicol acetyltransferase (CAT) gene. Following amplification, the 552 bp product was incubated in the presence or absence of two different preparations of anti-Taq antibodies prior to being digested with EcoRI and HindIII in the presence of $^{32}$P-dATP, and samples were then resolved on a 1% TBE-agarose gel followed by autoradiography. Lanes 1, 2, 6 and 7: no antibody treatment; lanes 3, 4 and 5: antibody preparation #1, at 1 unit, 0.67 unit and 0.33 unit, respectively; lanes 8, 9 and 10: antibody preparation #2, at 1 unit, 0.67 unit and 0.33 unit, respectively; lane 11: restriction enzyme digestion followed by treatment of samples with Klenow fragment (positive control).

In the description that follows, a number of terms conventionally used in the fields of molecular biology and protein engineering, and therefore generally understood by those of routine skill in the art, are utilized extensively. Certain terms as used herein, however, have specific meanings for the purposes of the present invention. In order to provide a clear and consistent understanding of the specification and claims, and the scope to be given such terms, the following definitions are provided.

The term "polypeptide" is used herein to mean a sequence of contiguous amino acids, of any length. As used herein, the terms "peptide" or "protein" may be used interchangeably with the term "polypeptide."

As used herein, "nucleotide" refers to a base-sugar-phosphate combination. Nucleotides are monomeric units of a nucleic acid sequence (DNA and RNA). The term nucleotide includes deoxyribonucleoside triphosphates ("dNTPs") such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates ("ddNTPs") and their derivatives, including, but not limited to, ddATP, ddCTP, ddGTP, ddITP, and ddTTP. In addition, the term nucleotide includes ribonucleoside triphosphates (rNTPs) such as rATP, rCTP, rITP, rUTP, rGTP, rTTP and their derivatives, which are analogous to the above-described dNTPs and ddNTPs except that the rNTPs comprise ribose instead of deoxyribose or dideoxyribose in their sugar-phosphate backbone. According to the present invention, a "nucleotide" may be unlabeled or detectably labeled by well known techniques. Detectable labels include, for example, radioactive isotopes, fluorescent labels, chemilurninescent labels, bioluminescent labels and enzyme labels.

The term "nucleic acid molecule" as used herein refers to a sequence of contiguous nucleotides (dNTPs or ddNTPs, or combinations thereof) which may encode a full-length polypeptide or a fragment of any length thereof, or which may be non-coding.

The term "dNTP" (plural "dNTPs") generically refers to the deoxynucleoside triphosphates (e.g., dATP, dCTP, dGTP, dTTP, dUTP, dITP, 7-deaza-dGTP, αdATP, αdTTP, αdGTP and αdCTP), and the term "ddNTP" (plural "ddNTPs") to their dideoxy counterparts, that are incorporated by polymerase enzymes into newly synthesized nucleic acids.

The term "unit" as used herein refers to the activity of an enzyme. When referring to a DNA polymerase, one unit of activity is the amount of enzyme that will incorporate 10 nanomoles of dNTPs into acid-insoluble material (i.e., DNA or RNA) in 30 minutes under standard primed DNA synthesis conditions.

The terms "stable" and "stability" as used herein generally mean the retention by an enzyme of at least 70%, preferably at least 80%, and most preferably at least 90%, of the original enzymatic activity (in units) after the enzyme or composition containing the enzyme has been stored for at least four weeks at a temperature of about 20–25° C., at least one year at a temperature of about 4° C. or at least 2 years at a temperature of −20° C.

As used herein, a "cloning vector" or "cloning vehicle" is a plasmid, cosmid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be spliced in order to bring about its replication and cloning. The cloning vector or vehicle may further contain a marker suitable for use in the identification of cells transformed with the cloning vector. Markers, for example, are tetracycline resistance or ampicillin resistance.

As used herein, a "primer" refers to a single-stranded oligonucleotide that is extended by covalent bonding of nucleotide monomers during amplification or polymerization of a DNA molecule The term "template" as used herein refers to a double-stranded or single-stranded nucleic acid molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof. The newly synthesized DNA molecule, according to the invention, may be equal or shorter in length than the original DNA template. Mismatch incorporation or strand slippage during the synthesis or extension of the newly synthesized DNA molecule may result in one or a number of mismatched base pairs. Thus, the synthesized DNA molecule need not be exactly complementary to the DNA template.

The term "incorporating" as used herein means becoming a part of a DNA molecule or primer.

As used herein, "amplification" refers to any in vitro method for increasing the number of copies of a nucleotide sequence with the use of a polymerase. Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR). One PCR reaction may consist of 5 to 100 "cycles" of denaturation and synthesis of a nucleic acid molecule.

An "oligonucleotide" as used herein refers to a synthetic or natural molecule comprising a covalently linked sequence of nucleotides which are joined by a phosphodiester bond between the 3' position of the pentose of one nucleotide and the 5' position of the pentose of the adjacent nucleotide.

As used herein, "thermostable" refers to an enzyme (such as a polypeptide having nucleic acid polymerase or reverse transcriptase activity) which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, the activities of T5 and T7 DNA polymerases are totally inactivated by exposing the enzymes to a temperature of 90° C. for 330 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation; thus heat treatment may reduce the DNA polymerase activity to some extent. A thermostable DNA polymerase typically will also have a higher optimum temperature than mesophilic DNA polymerases.

The terms "hybridization" and "hybridizing" as used herein refer to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In the present invention, the term "hybridization" refers particularly to hybridization of an oligonucleotide to a DNA template molecule.

"Working concentration" is used herein to mean the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent.

Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration of the reagent; and so on.

The terms "recombinase" and "recombination protein" as used herein may be used interchangeably, and refer to an exclusive or integrative protein, enzyme, co-factor or associated protein that is involved in recombination reactions involving one or more recombination sites, such as an enzyme which catalyzes the exchange of DNA segments at specific recombination sites. See, Landy, A., *Ann. Rev. Biochem.* 58:9133–949 (1989).

The terms "recognition sequence" or "recombination site" as used herein refer to a particular DNA sequence which a protein, DNA, or RNA molecule (e.g., a restriction endonuclease, a modification methylase, or a recombinase) recognizes and binds. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521–527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IHF, FIS, and Xis. See Landy, *Current Opinion in Biotechnology* 3:699–707 (1993). Such sites are also engineered according to the present invention to enhance methods and products.

The phrase "recombinational cloning" is used herein to mean a method whereby segments of DNA molecules are exchanged, inserted, replaced, substituted or modified, in vitro or in vivo.

Other terms used in the fields of recombinant DNA technology and molecular and cell biology as used herein will be generally understood by one of ordinary skill in the applicable arts.

Overview

The present invention is generally directed to methods that overcome the above-described temporal and economic constraints that are typically encountered during attempts to clone amplified or synthesized nucleic acid molecules. Thus, the invention provides methods that result in high-efficiency and rapid cloning of amplified, synthesized or digested nucleic acid molecules. Specifically, the methods of the invention entail the use of one or more inhibitors of nucleic acid polymerases in the cloning procedure, whereby residual polymerase activity remaining in the reaction mixture after amplification or synthesis is inactivated or inhibited. By the methods of the invention, amplified, synthesized or digested nucleic acid molecules may be quickly and efficiently ligated (using ligases, topoisomerases, etc.) into cloning vectors, and these vectors then inserted into host cells, for example for expression of the cloned nucleic acid molecules.

Methods according to this aspect of the invention may comprise one or more steps. One example is a method of cloning an amplified or synthesized nucleic acid molecule, comprising:

(a) amplifying or synthesizing one more nucleic acid molecules in the presence of one or more polypeptides having polymerase activity to produce amplified nucleic acid molecules; and (b) incubating the nucleic acid molecules with one or more inhibitors of the polypeptides having polymerase activity under conditions sufficient to inhibit or inactivate the polymerase activity.

Sources of Nucleic Acid Template Molecules

Using the methods of the invention, synthesized, amplified or digested nucleic acid molecules may be derived from a variety of sources. Nucleic acid molecules suitably cloned by the methods of the present invention may be DNA molecules (including cDNA molecules), RNA molecules (including polyadenylated RNA (polyA+ RNA), messenger RNA (mRNA), transfer RNA (tRNA) and ribosomal RNA (rRNA) molecules) or DNA-RNA hybrid molecules, and may be single-stranded or double-stranded.

The nucleic acid molecules to be cloned according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including those of species of the genera Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, and Streptomyces) or eukaryotic (including fungi (especially yeasts), plants, protozoans and other parasites, and animals including insects (particularly Drosophila spp. cells), nematodes (particularly *Caenorhabditis elegans* cells), and mammals (particularly human, rodent (rat or mice), monkey, ape, canine, feline, equine, bovine and ovine cells, and most particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells (e.g., embryonic stem cells). Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including HIV) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, F9 cells and the like. Other cells, cell lines, tissues, organs and organisms suitable as sources of nucleic acids for use in the present invention will be apparent to one of ordinary skill in the art.

In addition, such nucleic acid molecules and cDNA libraries may be obtained commercially, for example from Life Technologies, Inc. (Rockville, Md.) and other commercial suppliers that will be familiar to the skilled artisan.

Once the starting cells, tissues, organs, libraries or other samples are obtained, nucleic acid molecules to be cloned by the methods of the invention may be isolated by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). The nucleic acid molecules thus isolated may then be cloned using the methods of the present invention.

Amplified Nucleic Acid Molecules

Preferably, the nucleic acid molecules to be cloned are amplified nucleic acid molecules. Nucleic acid molecules may be amplified by a number of methods, which may comprise one or more steps. For example, one such method comprises (a) contacting a first nucleic acid molecule, a first primer molecule which is complementary to a portion of the first nucleic acid molecule, a second nucleic acid molecule and a second primer molecule which is complementary to a portion of the second nucleic acid molecule, with one or more polypeptides having polymerase activity; (b) incubating the molecules and one or more polypeptides under conditions sufficient to form a third nucleic acid molecule complementary to all or a portion of the first nucleic acid molecule and a fourth nucleic acid molecule complementary to all or a portion of the second nucleic acid molecule; (c) denaturing the first and third and the second and fourth nucleic acid molecules; and (d) repeating steps (a) through (c) one or more times. Such amplification methods may be accomplished by any of a variety of techniques, including but not limited to use of the polymerase chain reaction (PCR; U.S. Pat. Nos. 4,683,195 and 4,683,202), Strand Displacement Amplification (SDA; U.S. Pat. No. 5,455,166), and Nucleic Acid Sequence-Based Amplification (NASBA; U.S. Pat. No. 5,409,818); particularly preferred is PCR.

In another aspect, the invention relates to the above-described nucleic acid synthesis or amplification methods, wherein the first and/or second primer nucleic acid molecules used in the above-described amplification methods comprise one or more recombination sites (recombinase recognition sites) or portions thereof. Nucleic acid molecules synthesized or amplified according to this aspect of the invention thus will comprise one or more recombination sites or portions thereof, thereby facilitating easy movement or exchange of nucleic acid segments between different synthesized nucleic acid molecules using one or more recombinase proteins in a process termed recombinational cloning, as described below. Preferred combinations of recombination sites/recombination proteins for use according to this aspect of the invention include the Integrase/att system from bacteriophage λ (Landy, A. (1993) *Current Opinions in Genetics and Devel.* 3:699–707); the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109); the FLP/FRT system from the *Saccharomyces cerevisiae* 2μ circle plasmid (Broach et al. *Cell* 29:227–234 (1982); the resolvase family (e.g., γδ, Tn3 resolvase, Hin, Gin, and Cin) (Maeser and Kahnmann (1991) *Mol. Gen. Genet.* 230:170–176); and site-specific recombination proteins encoded by bacteriophage lambda, phi 80, P22, P2, 186, P4 and P1. Methods for preparation of primers comprising one or more recombination sites, and use of such primers in synthesizing or amplifying one or more nucleic acid molecule products which comprise one or more recombination sites, are described in detail in commonly owned, co-pending U.S. application Ser. Nos. 08/486,139, filed Jun. 7, 1995; 60/065,930, filed Oct. 24, 1997; and 09/005,476, filed Jan. 12, 1998, the disclosures of all of which are incorporated herein by reference in their entireties.

In one embodiment of the present invention, the amplified nucleic acid fragments may be cloned (ligated) directly into one or more vectors to produce one or more genetic constructs. The genetic constructs may then be transformed into one or more host cells.

In other cloning methods, amplified molecules cleaved or digested with one or more restriction enzymes or one or more recombination proteins as described in more detail below can be cloned into appropriate insertion sites of cloning vectors (see, e.g., Ausubel, F. M., et al., eds., "Current Protocols in Molecular Biology," New York: John Wiley & Sons, Inc., pp. 3.16.1–3.16.11 (1995)). Restriction enzymes used for cleavage of the amplified molecules may include blunt-end cutters (e.g., SmaI, SspI, ScaI, etc.) and sticky-end cutters (e.g., HindIII, BamHI, KpnI, etc.). Amplified nucleic acid molecules can also be cloned using uracil DNA glycosylase (UDG; see U.S. Pat. No. 5,137,814, which is incorporated herein by reference in its entirety).

In another aspect of the invention, restriction enzyme sites can be incorporated into the amplification primers; the amplified nucleic acid molecules will thus contain these restriction sites. For cloning of these specific sequences, these amplified nucleic acid molecules can then be digested with restriction enzymes, the digested fragments ligated into an appropriate site within a plasmid vector, and the vector incorporated into a host cell as described in more detail below.

In another aspect of the invention, recombination or recombinase recognition sites can be incorporated into the amplification primers; the amplified nucleic acid molecules will thus contain these recombination or recombinase recognition sites. These amplified nucleic acid molecules can then be treated with one or more recombinations proteins as described below, to facilitate exchange or recombination of one or more nucleic acid segments between different amplified nucleic acid molecules, in a process known as recombinational cloning. The resulting recombined nucleic acid molecules may then be inserted into a plasmid vector, and the vector incorporated into a host cell as described in more detail below.

Amplified products generated by DNA polymerases which incorporate an additional deoxyadenosine (dA) residue at the 3' termini of the products (e.g., Taq DNA polymerase), can be cloned into specific cloning vectors containing 3' deoxythymidine (dT) overhangs which provide a specific recognition sequence for the 3' A residue on the amplified product. This process, often referred to as "TA cloning," provides a means of directly cloning amplified nucleic acid molecules without the need for preparation of primers with specific restriction sites (see U.S. Pat. No. 5,487,993, which is incorporated herein by reference in its entirety). Alternatively, a ligase-independent strategy for cloning may be used (such as Topo-TA Cloning®; Invitrogen, Carlsbad, Calif.). Blunt-end cloning of such amplified molecules containing dA overhangs may be facilitated by using T4 DNA polymerase to remove the dA overhangs (a procedure often termed "polishing") followed by insertion of the resulting blunt-end fragments into blunt-end vector insertion sites as described in more detail below.

Polymerases and Reverse Transcriptases

A variety of polypeptides having polymerase activity are useful in the methods of the present invention. Included among these polypeptides are enzymes such as nucleic acid polymerases (including DNA polymerases and RNA polymerases), as well as polypeptides having reverse transcriptase (i.e., RNA-dependent DNA polymerase) activity.

Polypeptides having reverse transcriptase activity that may be advantageously used in the present methods include, but are not limited to, Moloney Murine Leukemia Virus (M-MLV) reverse transcriptase, Rous Sarcoma Virus (RSV) reverse transcriptase, Avian Myeloblastosis Virus (AMV) reverse transcriptase, Rous-Associated Virus (RAV) reverse transcriptase, Myeloblastosis Associated Virus (MAV) reverse transcriptase, Human Immunodeficiency Virus (HIV) reverse transcriptase, retroviral reverse transcriptase, retrotransposon reverse transcriptase, hepatitis B reverse transcriptase, cauliflower mosaic virus reverse transcriptase, bacterial reverse transcriptase, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT®) DNA polymerase, *Pyrococcus furiosus* (Pfu) DNA polymerase, DEEP-VENT™ Pyrococcus species GB-D DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfoloblus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants and derivatives thereof. Particularly preferred for use in the invention are the variants of these enzymes that are substantially reduced in RNase H activity (i.e., "RNase H⁻" enzymes). By an enzyme "substantially reduced in RNase H activity" is meant that the enzyme has less than about 20%, more preferably less than about 15%, 10% or 5%, and most preferably less than about 2%, of the RNase H activity of a wildtype or "RNase H⁺" enzyme such as wildtype M-MLV or AMV reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988) and in Gerard, G. F., et al., *FOCUS* 14(5):91 (1992), the disclosures of all of which are fully incorporated herein by reference. Particularly preferred RNase H⁻ reverse transcriptase enzymes for use in the invention include, but are not limited to, M-MLV H⁻ reverse transcriptase, RSV H⁻ reverse transcriptase, AMV H⁻ reverse transcriptase, RAV H⁻ reverse transcriptase, MAV H⁻ reverse transcriptase and HIV H⁻ reverse transcriptase. It will be understood by one of ordinary skill, however, that any enzyme capable of producing a DNA molecule from a ribonucleic acid molecule (i.e., having reverse transcriptase activity) that is substantially reduced in RNase H activity may be equivalently used in the compositions, methods and kits of the invention.

Enzymes used in the invention may have distinct reverse transcription pause sites with respect to the template nucleic acid. Whether or not two enzymes have distinct reverse transcription pause sites may be determined by a variety of assays, including, for example, electrophoretic analysis of the chain lengths of DNA molecules produced by the two enzymes (Weaver, D. T., and DePamphilis, M. L., *J. Biol. Chem.* 257(4):2075–2086 (1982); Abbots, J., et al., *J. Biol. Chem.* 268(14):10312–10323 (1993)), or by other assays that will be familiar to one of ordinary skill in the art. As described above, these distinct transcription pause sites may represent secondary structural and sequence barriers in the nucleic acid template which occur frequently at homopolymer stretches. Thus, for example, the second enzyme may reverse transcribe to a point (e.g., a hairpin) on the template nucleic acid that is proximal or distal (i.e., 3' or 5') to the point to which the first enzyme reverse transcribes the template nucleic acid. This combination of two or more enzymes having distinct reverse transcription pause sites facilitates production of full-length cDNA molecules since the secondary structural and sequence barriers may be overcome.

Polypeptides having reverse transcriptase activity for use in the invention may be obtained commercially, for example from Life Technologies, Inc. (Rockville, Md.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, the polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372–3376 (1988)).

Nucleic acid polymerases such as DNA polymerases for use in the present methods may be isolated from natural or recombinant sources, by techniques that are well-known in the art (See WO 92/06200, U.S. Pat. Nos. 5,455,170 and 5,466,591, WO 96/10640 and U.S. patent application Ser. No. 08/370,190, filed Jan. 9, 1995, U.S. Pat. No. 5,912,155), from a variety of thermophilic bacteria that are available commercially (for example, from American Type Culture Collection, Rockville, Md.) or may be obtained by recombinant DNA techniques (see, e.g., WO 96/10640 and U.S. patent application Ser. No. 08/370,190, filed Jan. 9, 1995, U.S. Pat. No. 5,912,155). Suitable for use as sources of thermostable polymerases or the genes thereof for expression in recombinant systems are the thermophilic bacteria *Thermus thermophilus, Thermococcus litoralis, Pyrococcus furiosus, Pyrococcus woosii* and other species of the Pyrococcus genus, *Bacillus sterothermophilus, Sulfolobus acidocaldarius, Thermoplasma acidophilum, Thermus flavus, Thermus ruber, Thermus brockianus, Thermotoga neapolitana, Thermologa maritima* and other species of the Thermotoga genus, and *Methanobacterium thermoautotrophicum*, and mutants, variants or derivatives thereof. It is to be understood, however, that thermostable DNA polymerases from other organisms may also be used in the present invention without departing from the scope or preferred embodiments thereof. As an alternative to isolation, thermostable DNA polymerases are available commercially from, for example, Life Technologies, Inc. (Rockville, Md.), New England BioLabs (Beverly, Mass.), Finnzymes Oy (Espoo, Finland), Stratagene (La Jolla, Calif.), Boehringer Mannheim Biochemicals (Indianapolis, Ind.) and Perkin Elmer Cetus (Norwalk, Conn.).

DNA polymerases used in accordance with the invention may be any enzyme that can synthesize a DNA molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT® Tli and DEEPVENT™ Pyrococcus Species GB-D DNA polymerases, and mutants, variants and derivatives thereof (U.S. Pat. No. 5,436,149; U.S. Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M., et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Barnes, W. M., *Gene* 112:29–35 (1992); and co-pending U.S. patent application Ser. No. 08/689,815, filed Feb. 14, 1997, now abandoned, the disclosures of which are incorporated herein in their entireties. Examples of DNA polymerases substantially lacking in 3' exonuclease activity include, but are not limited to, Taq, Tne(exo⁻), Tma(exo⁻), Pfu(exo⁻) Pwo(exo⁻) and Tth DNA polymerases, and mutants, variants and derivatives thereof. Nonlimiting examples of DNA polymerases having 3' exonuclease activity include Pfu, DEEPVENT™ Pyrococcus Species GB-D DNA polymerase, Tli/VENT®, Tne, Tma, and mutants, variants and derivatives thereof.

Polypeptides having nucleic acid polymerase and/or reverse transcriptase activity are preferably used in the present methods at a final concentration in solution of about 0.1–200 units per milliliter, about 0.1–50 units per milliliter, about 0.1–40 units per milliliter, about 0.1–36 units per milliliter, about 0.1–34 units per milliliter, about 0.1–32 units per milliliter, about 0.1–30 units per milliliter, or about 0.1–20 units per milliliter, and most preferably at a concentration of about 20 units per milliliter. Of course, other suitable concentrations of reverse transcriptase enzymes and nucleic acid polymerases suitable for use in the invention will be apparent to one of ordinary skill in the art.

Cloning of Nucleic Acid Molecules

The methods of the invention may further comprise one or more additional steps designed to facilitate the cloning of the amplified or synthesized nucleic acid molecules. For example, nucleic acid molecules amplified or synthesized as described above may be digested with one or more restriction endonucleases, to produce a collection of digested nucleic acid molecules. Suitable methods and enzymes for use in digesting nucleic acid molecules will be familiar to one of ordinary skill in the art (see, e.g., Sambrook, J., et al., *Molecular Cloning: A Laboratory Manual*, 2nd ed., Cold Spring Harbor, N.Y.: Cold Spring Harbor Laboratory Press (1989)). Restriction endonucleases that may be advantageously used in the methods of the invention include, but are not limited to, AluI, Eco47 III, EcoRV, FspI, HpaI, MscI, NruI, PvuII, RsaI, ScaI, SmaI, SspI, StuI, ThaI, AvaI, BamHI, BanII, BglII, ClaI, EcoRI, HindIII, HpaII, KpnI, MseI, NcoI, NdeI, NotI, PstI, PvuI, SacI/SstI, SalI, XbaI, XhoI and I-CeuI. Such restriction endonucleases are available commercially, for example from Life Technologies, Inc. (Rockville, Md.), Sigma (St. Louis, Mo.) and New England BioLabs (Beverly, Mass.). Topoisomerases or other nucleic acid-modifying enzymes may also be used.

In alternative cloning methods of the invention, amplified nucleic acid molecules that comprise one or more recombination sites may be treated with one or more recombination proteins which recognize, bind to, and cleave the nucleic acid molecules at the specific recombination sites. Preferred recombination proteins for use in this aspect of the invention include those described above, such as the Int, IHF or Xis integrases; Cre; γδ, Tn3 resolvase, Hin, Gin, Cin, Flp; and other recombination proteins encoded by bacteriophage λ, phi 80, P22, P2, 186, P4 and P1. Appropriate methods using such recombination proteins in cloning of nucleic acid molecules comprising one or more recombination sites are described in detail in commonly owned, co-pending U.S. application Ser. Nos. 08/486,139, filed Jun. 7, 1995; 60/065, 930, filed Oct. 24, 1997; and 09/005,476, filed Jan. 12, 1998, the disclosures of all of which are incorporated herein by reference in their entireties.

Once the synthesized or amplified nucleic acid molecules have been digested with one or more restriction enzymes or cleaved with one or more recombination proteins, the digested or cleaved nucleic acid molecules may be inserted (typically by ligation, for example using a polypeptide having nucleic acid ligase activity such as T4 DNA ligase, topoisomerase or the like) into one or more vectors, such as one or more expression vectors, to yield one or more genetic constructs. Alternatively, the amplified or synthesized nucleic acid molecules may be ligated directly into one or more vectors without being digested or cleaved, to form one or more genetic constructs. Genetic constructs according to this aspect of the invention thus typically comprise the amplified, synthesized or digested/cleaved nucleic acid molecule (or fragments thereof) and the vector or cloning vehicle. These genetic constructs may, in turn, be introduced into host cells using well-known techniques such as infection, transduction, transfection, electroporation and transformation, for the large-scale production of cDNA libraries or plasmids comprising the amplified, synthesized or digested/cleaved nucleic acid molecules, or for the expression of the amplified, synthesized or digested/cleaved nucleic acid molecules. The vectors may be, for example, a phage, plasmid, viral or retroviral vector, and is preferably an expression vector as described below. Retroviral vectors may be replication-competent or replication-defective. In the latter case, viral propagation generally will occur only in complementing host cells.

The polynucleotides may be joined to a vector containing a selectable marker for propagation in a host. Generally, a plasmid vector is introduced into mammalian or avian cells in a precipitate, such as a calcium phosphate precipitate, or in a complex with a charged lipid (e.g., LIPOFECTAMINE™; Life Technologies, Inc.; Rockville, Md.) or in a complex with a virus (such as an adenovirus; see U.S. Pat. Nos. 5,547,932 and 5,521,291) or components of a virus (such as viral capsid peptides). If the vector is a virus, it may be packaged in vilro using an appropriate packaging cell line and then transduced into host cells.

Preferred are vectors comprising cis-acting control regions to the nucleic acid molecule of interest. Appropriate trans-acting factors may be supplied by the host, by a complementing vector or by the vector itself upon introduction into the host.

In certain preferred embodiments in this regard, the vectors may provide for specific expression of the amplified, synthesized or digested/cleaved nucleic acid molecules, which may be inducible and/or cell type-specific. Particularly preferred among such expression vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophages, yeast episomes, yeast chromosomal elements, viruses such as baculoviruses, papovaviruses, λ phage, vaccinia viruses, adenoviruses, fowl pox viruses, pseudorabies viruses and retroviruses, and vectors derived from combinations thereof, such as cosmids and phagemids.

In one embodiment, an isolated nucleic acid molecule of the invention or fragment thereof may be operably linked to an appropriate regulatory sequence, preferably a promoter such as the phage lambda PL promoter, promoters from T3, T7 and SP6 phages, the *E. coli* lac, trp and tac promoters, the SV40 early and late promoters and promoters of retroviral LTRs and derivatives thereof, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiation codon (AUG) at the beginning and a termination codon (UAA, UGA or UAG) appropriately positioned at the end of the polypeptide to be translated.

As indicated above, the expression vectors will preferably include at least one selectable marker. Such markers include dihydrofolate reductase (dhfr) or neomycin (neo) resistance for eukaryotic cell culture and tetracycline (tet) or ampicillin (amp) resistance genes for culturing in *E. coli* and other bacteria. Representative examples of appropriate hosts include, but are not limited to, bacterial cells, such as Escherichia spp. cells (particularly *E. coli*), Bacillus spp. cells (particularly *B. cereus, B. subtilis* and *B. megaterium*), Streptomyces spp. cells, Salmonella spp. cells (particularly *S. typhimurium*) and Xanthomonas spp. cells; fungal cells, including yeast cells such as Saccharomyces spp. cells; insect cells such as Drosophila S2, Spodoptera Sf9 or Sf21 cells and Trichoplusa High-Five cells; other animal cells (particularly mammalian cells and most particularly human cells) such as CHO, COS, VERO, HeLa, Bowes melanoma cells and HepG2 and other liver cell lines; and higher plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A and pNH46A, available from Stratagene; pcDNA3 available from Invitrogen; and pGEX, pTrxfus, pTrc99a, pET-5, pET-9, pKK223-3, pKK233-3, pDR540 and pRIT5 available from Pharmacia. Among preferred eukaryotic vectors are pWLNEO, pSV2CAT, pOG44, pXT1, pBK and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3, T7 and SP6 phage promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the genetic constructs into the host cells can be effected by a variety of methods, such as calcium phosphate transfection, DEAE-dextran mediated transfection, cationic lipid-mediated transfection, electroporation, transduction, infection, nucleic acid-coated microprojectile bombardment or other methods. Such methods are described in many standard laboratory manuals, such as Davis et al., *Basic Methods In Molecular Biology* (1986).

Thus, the invention further provides, in an additional embodiment, a method of ligating an amplified nucleic acid molecule into a vector with increased efficiency. Such methods may comprise one or more steps, such as (a) forming a mixture comprising one or more of the above-described nucleic acid molecules and one or more polymerase inhibitors; and (b) ligating the nucleic acid molecules into one or more of the above-described vectors to form one or more genetic constructs. Analogously, the invention also provides methods suitable for cloning a nucleic acid molecule, such as those described above, into one or more of the above-described vectors. An exemplary method may comprise (a) forming a mixture comprising the nucleic acid molecules to be cloned, the cloning vectors and one or more polymerase inhibitors; and (b) ligating the nucleic acid molecules into one or more of the above-described vectors to form one or more genetic constructs. In an additional embodiment, the invention provides a further method of cloning nucleic acid molecules, such as those described above, into one or more vectors comprising: (a) forming a mixture comprising the nucleic acid molecules to be cloned, one or more polymerase inhibitors and one or more of the above-described restriction endonucleases; and (b) ligating the nucleic acid molecules into one or more of the above-described vectors to form one or more genetic constructs. In an additional embodiment, the invention provides a further method of cloning nucleic acid molecules, such as those described above, into one or more vectors comprising: (a) forming a mixture comprising the nucleic acid molecules to be cloned, one or more polymerase inhibitors and one or more of the above-described recombination proteins; and (b) ligating the nucleic acid molecules into one or more of the above-described vectors to form one or more genetic constructs.

According to the invention, the mixture formed in the steps (a) of the above-described methods may further comprise one or more additional components, including but. not limited to one or more of the above-described polypeptides having polymerase activity, one or more dNTPs or ddNTPs, one or more polypeptides having reverse transcriptase activity, one or more buffer salts, and the like. In one of the above aspects of the invention, the polypeptides having polymerase activity and the one or more restriction endonucleases or one or more recombination proteins may be added to the mixture simultaneously. In another of the above aspects, the polymerases and endonucleases or recombinases may be added sequentially, in any order. These methods of the invention may also further comprise one or more additional steps, such as the transformation of one or more of the genetic constructs formed by these methods into one or more of the above-described host cells.

These methods of the invention may be advantageously used to clone or ligate any nucleic acid molecule, which may be an amplified nucleic acid molecule, into a vector and/or host cell. Thus, the invention also provides nucleic acid molecules cloned by such methods, and host cells produced by being transformed with the above-described cloned nucleic acid molecules according to the methods of the invention.

Polymerase Inhibitors

As described above, the methods of the invention (particularly the cloning and ligation methods) advantageously utilize one or more inhibitors of the polymerase activity of the polypeptides used to amplify the nucleic acid molecules.

As used herein, an "inhibitor" of a polymerase is defined as any compound, composition or combination thereof that inactivates or reduces the activity of a polypeptide having nucleic acid polymerase activity, reversibly or irreversibly. In particular, inhibitors of a polymerase as used in the present invention will, upon contact with or binding to the polymerase polypeptide, reduce the activity of the polypeptide to no greater than about 70%, 60%, 50%, 40%, 30%, 20%, 10%, 9%, 8%, 7%, 6%, 5%, 4%, 3%, 2% 1% or 0.1%, of the activity of a polypeptide having polymerase activity (such as those described above) that has not been contacted with the inhibitor. As a practical matter, whether a particular inhibitor reduces the activity to no greater than about 70%, 60%, 50%, 40%, 30%, 20%, 10%, 9%, 8%, 7%, 6%, 5%, 4%, 3%, 2% 1% or 0.1%, of the activity of an uninhibited polypeptide having polymerase activity, may be determined by measuring the unit activity (by the methods described above and others that will be familiar to one of ordinary skill) of the polymerase in the presence and absence of various concentrations of the inhibitor.

A variety of inhibitors are suitable for use in the present methods. Included among these inhibitors are antibodies that bind to the above-described polypeptides having polymerase activity (such as anti-Taq antibodies, anti-Tne antibodies, anti-Tma antibodies or anti-Pfu antibodies), and fragments thereof (such as Fab or Fab'$_2$ fragments). Such antibodies may be polyclonal or monoclonal, and may be prepared in a variety of species according to methods that are well-known in the art. See, for instance, Sutcliffe, J. G., et al., *Science* 219:660–666 (1983); Wilson et al., *Cell* 37: 767 (1984); and Bittle, F. J., et al., *J. Gen. Virol.* 66:2347–2354 (1985). Antibodies specific for any of the above-described polymerases, such as anti-Taq antibodies, anti-Tne antibodies, anti-Tma antibodies and anti-Pfu antibodies, can be raised against the intact polymerase polypeptide or one or more antigenic polypeptide fragments thereof. These polypeptides or fragments may be presented together with a carrier protein (e.g., albumin) to an animal system (such as rabbit or mouse) or, if they are long enough (at least about 25 amino acids), without a carrier.

As used herein, the term "antibody" (Ab) may be used interchangeably with the terms "polyclonal antibody" or "monoclonal antibody" (mAb), except in specific contexts as described below. These terms, as used herein, are meant to include intact molecules as well as antibody fragments (such as, for example, Fab and F(ab')$_2$ fragments) which are capable of specifically binding to a polypeptide having polymerase activity (such as a thermostable DNA polymerase or a reverse transcriptase) or a portion thereof.

The anti-polymerase antibodies used in the methods of the present invention may be polyclonal or monoclonal, and may be prepared by any of a variety of methods (see, e.g., U.S. Pat. No. 5,587,287). For example, polyclonal antibodies may be made by immunizing an animal with one or more polypeptides having polymerase activity or portions thereof (e.g., one or more thermostable DNA polymerases such as Taq, Tne, Tma or Pfu polymerase) according to standard techniques (see, e.g., Harlow, E., and Lane, D., *Antibodies: A Laboratory Manual*, Cold Spring Harbor, N.Y.: Cold Spring Harbor Laboratory Press (1988); Kaufman, P. B., et al., In: *Handbook of Molecular and Cellular Methods in Biology and Medicine*, Boca Raton, Fla.: CRC Press, pp. 468–469 (1995)). Alternatively, anti-polymerase monoclonal antibodies (or fragments thereof), such as anti-DNA polymerase antibodies (e.g., anti-Taq, anti-Tne, anti-Tma or anti-Pfu antibodies) to be used in the present methods may be prepared using hybridoma technology that is well-known in the art (Köhler et al., *Nature* 256:495 (1975); Köler et al., *Eur. J. Immunol.* 6:511 (1976); Köhler et al., *Eur. J. Immunol.* 6:292 (1976); Hammerling et al., In: *Monoclonal Antibodies and T-Cell Hyhridomas*, New York: Elsevier, pp. 563–681 (1981); Kaufman, P. B., et al., In: *Handbook of Molecular and Cellular Methods in Biology and Medicine*, Boca Raton, Fla.: CRC Press, pp. 444–467 (1995)).

In yet another approach, antibodies capable of binding to one or more polypeptides having polymerase activity, or fragments thereof, may be used to remove the polypeptides having polymerase activity, thus preventing the polymerase from having an adverse effect on cloning of the amplified molecule. In such a procedure, antibodies (or fragments thereof) specific for the polymerase may be used to remove the polymerase from the reaction. Alternatively, the anti-polymerase antibody may be used to inhibit/inactivate the polymerase and a second antibody specific for the anti-polymerase antibody can be used to remove the inactivated polymerase.

It will be appreciated that Fab, F(ab')$_2$ and other fragments of the above-described antibodies may be used in the methods described herein. Such fragments are typically produced by proteolytic cleavage, using enzymes such as papain (to produce Fab fragments) or pepsin (to produce F(ab')$_2$ fragments). Polymerase-binding antibody fragments may also be produced through the application of recombinant DNA technology or through synthetic chemistry.

Alternatively, antibodies directed against one or more of the above-described polypeptides having polymerase activity, which may be used to inhibit the activity of residual polymerases in the reaction mixture following amplification of nucleic acid molecules, may be obtained commercially for example from Life Technologies, Inc. (Rockville, Md.), Boehringer Mannheim (Indianapolis, Ind.) and Sigma (St. Louis, Mo.).

In addition to antibodies, other compounds that are suitable as inhibitors for use in the present methods include chemicals, which may be synthetic or naturally occurring (such as α-amanatin, polyethylene glycol, dimethylsulfoxide, formamide, dimethylformamide, urea, pyrophosphate, acetic anhydride and diethylpyrocarbonate), antibiotics (such as actinomycin-D), heavy metals (such as compounds containing nickel (particularly Ni$^{++}$-containing salts) or copper (particularly Cu$^{++}$-containing salts)), acids (such as digallic acid, aurochloric acid, phosphonoformate and podoscyphic acid), metal chelators (such as EDTA), nucleotide analogues (such as peptide nucleic acid (PNA) and 2-(p-n-butylanilino)-dATP), sulfhydryl reagents (such as n-ethylmaleimide or iodoacetic acid), anionic detergents (such as sodium dodecylsulfate), polyanions (such as spermidine), captan ((N-[trichloromethyl]-thio)-4-cyclohexene-1,2-dicarboximide), acidic polysaccharides (such as dextran sulfate and heparin), a binding protein or peptide, and combinations thereof. However, it will be understood by the skilled artisan that any compound, natural or synthetic, that inhibits or inactivates the polymerase activity of a polypeptide according to the above parameters may be advantageously used in the methods of the present invention.

In use, the one or more inhibitors function to increase the efficiency of cloning of the above-described amplified, synthesized or digested nucleic acid molecules. It is thought that such an advantage is due to the action of the inhibitors to prevent or inhibit modification of one or more of the termini (3' and/or 5') of the amplified, synthesized or digested nucleic acid molecules; it will be understood, however, that regardless of the mechanism of action the one or more inhibitors functions to provide increased efficiency of cloning of the amplified, synthesized and digested nucleic acid molecules.

Compositions

In an another embodiment, the present invention is directed to compositions which may be used, for example, in the methods of the present invention to clone an amplified nucleic acid molecule. Compositions of the invention may comprise one or more components, which may be present in solution or in solid form, and which may be formulated at working concentrations or in solutions of higher concentration (for example, 2×, 2.5×, 5×, 10×, 20×, 25×, 50×, 100×, 250×, 500×, 1000× and the like).

A preferred composition of the invention comprises one or more of the above-described restriction endonucleases and one or more of the above-described polymerase inhibitors. These restriction endonucleases and polymerase inhibitors may be present at the working concentrations noted above, or at higher than working concentrations, and may each be present at different concentrations. In particularly preferred compositions of the invention, the restriction endonucleases and polymerase inhibitors are stable upon storage, such that the compositions themselves may be stored for extended periods of time without losing activity. As noted above, the term "stable" as used herein means that the restriction endonucleases and polymerase inhibitors that make up the present compositions retain at least 70%, preferably at least 80%, and most preferably at least 90%, of their original enzymatic activity (in units) after the composition containing the enzyme has been stored for at least four weeks at a temperature of about 20–25° C., at least one year at a temperature of about 4° C. or at least 2 years at a temperature of –20° C.

Alternative compositions of the invention may comprise one or more polymerase inhibitors, such as those described above, and may optionally further comprise one or more additional components, for example, one or more DNA-modifying enzymes or combinations thereof (such as ligases, topoisomerases, kinases, phosphatases, nucleases, endonucleases, terminal deoxynucleotidyl transferases, etc.).

The compositions of the invention may additionally comprise one or more nucleic acid molecules (including amplified nucleic acid molecules or fragments or derivatives thereof), one or more nucleotides (including dNTPs, ddNTPs and/or rNTPs), one or more detergents (including TRITON X-100®, Nonidet P-40 (NP-40), Tween 20, Brij 35, sodium deoxycholate or sodium dodecylsulfate), one or more enzyme cofactors and/or one or more suitable buffers (such as TRIS, phosphate salts (such as sodium phosphate (mono- or dibasic) and potassium phosphate), sodium bicarbonate, sodium acetate, HEPES, and the like). Combinations of ammonium sulfate, one or more magnesium salts (such as magnesium chloride or magnesium sulfate), one or more manganese salts (such as manganese sulfate) and potassium chloride (or other salts), may also be used in formulating the compositions of the present invention. A small amount of a salt of ethylenediaminetetraacetate (EDTA) may also be added (preferably about 0.1 millimolar), although inclusion of EDTA does not appear to be essential to the function or stability of the compositions of the present invention. Other components that may advantageously be added to the present compositions to facilitate their use in cloning of amplified nucleic acid molecules will be apparent to the skilled artisan.

Following formulation, the present compositions may be filtered through a low protein-binding filter unit that is available commercially (for example from Millipore Corporation, Bedford, Mass.) and stored until use. To reduce component denaturation, storage of the present compositions is preferably in conditions of diminished light, e.g., in amber or otherwise opaque containers or in storage areas with controlled low lighting. The compositions of the present invention are unexpectedly stable at ambient temperature (about 20°–25° C.) for about 4–10 weeks, are stable for at least one year upon storage at 4° C., and for at least two years upon storage at –20° C. Surprisingly, storage of the compositions at temperatures below freezing (e.g., –20° C. to –70° C.), as is traditional with stock solutions of bioactive components, is not necessary to maintain the stability of the compositions of the present invention.

Kits

In another embodiment, the invention relates to kits for cloning an amplified nucleic acid molecule. Kits according to the present invention may comprise a carrier means, such as a box, carton, tube or the like, having in close confinement therein one or more containers, such as vials, tubes, ampules, bottles and the like. A first container in the present kits may contain, for example, one or more of the above-described polymerase inhibitors. The kits of the invention may further comprise one or more additional containers containing one or more additional reagents and compounds, such as one or more polypeptides having polymerase activity, one or more primers, one or more nucleotides (such as dNTPs, ddNTPs and/or rNTPs), one or more polypeptides having reverse transcriptase activity, one or more nucleic acid-modifying enzymes (such as topoisomerases, ligases, phosphatases, etc.), one or more vectors, one or more host cells (particularly one or more of the above-described host cells and most particularly one or more transformation-competent host cells), one or more restriction endonucleases, and one or more recombination proteins. Additional kits of the invention may comprise one or more of the above-described compositions of the invention. These kits and their components are preferably stable upon storage according to the above-described parameters of stability, and may be advantageously used to clone a nucleic acid molecule, preferably an amplified nucleic acid molecule, according to the methods of the invention.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Inhibition of Polymerase Activity Facilitates Cloning of Amplified Nucleic Acid Molecules In initial experiments, the amount of polymerase activity remaining in a PCR reaction mixture after amplification was determined. The activity of Taq DNA polymerase remaining after 30 cycles of PCR was assayed directly by the standard unit assay (Innis, M. A., et al., *Proc. Natl. Acad. Sci. USA* 85:9436–9440 (1988); Gelfand, D. H., in: *Current Commu-* nications in *Molecular Biology: Polyrnerase Chain Reaction*, Ehrlich, H., et al., eds., Cold Spring Harbor, N.Y.: Cold Spring Harbor Laboratory, pp. 11–17 (1989)), using several sources of polymerase: Native Taq (Life Technologies, Inc.), Elongase enzyme mix (Life Technologies, Inc.) and AmpliTaq (Perkin-Elmer). The results of these experiments indicated that after 30 cycles of PCR, 60–96% of the initial Taq activity remained (data not shown), which was sufficient Taq activity to perform another 30 cycles of PCR. These findings therefore confirmed those previously reported (Bennett, B. L., and Molenaar, A. J., *BioTechniques* 16(1):36–37 (1994).

To determine if elimination of this polymerase activity facilitated cloning of the amplification products, a series of experiments was conducted. PCR primers were designed to amplify out a 664-bp fragment within the pPROEX-CAT cloning vector (Life Technologies, Inc.) which encodes a gene for chloramphenicol acetyl transferase (CAT) and confers chloramphenicol resistance on transformants containing the gene. The upstream (5') primer was located near an EcoRI site in the CAT coding region and the downstream (3') primer bound to a region 3' to the CAT gene past a unique HindIII site. The experiments consisted of Taq polymerase-mediated amplification of the plasmid insert, followed by various methods of Taq removal prior to digestion of the termini of the PCR products with EcoRI and HindIII. Because of extra nucleotide sequence contributions from the primer design, the actual PCR product was 664 bp which generated a 522-bp fragment after digestion. The digested PCR product was then gel purified by electroelution prior to quantitation and ligation into an ampicillin-resistant pPROEX-CAT cloning vector that had been similarly digested with EcoRI and HindIII. This experimental design therefore provided for direct detection of the number of transformants (i.e., the number of ampicillin-resistant ("amp$^r$") colonies) and whether the insert was correctly ligated, in-frame, into the vector in these transformants. Specifically, if the insert was correctly ligated, the ampicillin-resistant bacterial colonies would also be resistant to chloramphenicol ("cam$^r$") in the presence of IPTG, which would induce expression of the CAT gene in the insert. This assay also provided a means of identifying whether the residual Taq polymerase had partially or completely filled in the restriction enzyme-generated cohesive ends on the amplicon: partial fill-in of termini by Taq prior to ligation would shift the reading frame of the ligated insert and result in improper transcription of the CAT gene and loss of chloramphenicol resistance (i.e., colonies would be observed that were amp$^r$ but not cam$^r$).

To serve as a positive control for this experiment, the plasmid pPROEX-CAT was digested with EcoRI and HindIII prior to agarose gel electrophoresis and purification of each of the two generated DNA fragments. The purified vector and insert fragments were religated in a 1:1 molar ratio; this preparation served as a positive control since neither fragment was exposed to Taq DNA polymerase. The negative control consisted of a "vector-only" ligation reaction.

The 664-bp fragment was amplified using the pPROEX-CAT vector as a template in a series of amplification reactions such that the total reaction volume was equivalent to 5 ml. After confirmation of successful amplification of the 664-bp fragment by agarose gel analysis and EtBr-staining, all of the reactions were pooled to minimize sample variation that may have taken place during PCR which could potentially bias the cloning results. This pool was then resplit into several aliquots to undergo post-PCR manipulations, designed to reduce or eliminate residual Taq polymerase prior to cloning, as follows:

a.) Ethanol precipitation: A 600 µl aliquot of the reaction pool was precipitated with ethanol in the presence of sodium acetate, followed by digestion of the precipitate with EcoRI and HindIII in React 2 buffer. Following RE-digestion, the sample was extracted once with phenol/chloroform/isoamyl alcohol (25:24:1) followed by an additional 100% chloroform extraction. The sample was then subjected to electrophoresis on a 1% agarose gel, followed by EtBr staining and excision of the 564-bp fragment. The DNA was recovered from the gel slice by electroelution, ethanol precipitated again, resuspended in TE buffer or sterile water and then a portion of it was visually quantitated on an agarose gel by EtBr-staining compared to similarly stained standards.

b.) Gel Purification: A 600 µl aliquot of the PCR pool was subjected to agarose-gel electrophoresis and EtBr-staining and was recovered from the gel by using a GlassMAX procedure according to the manufacturer's instructions (Life Technologies, Inc.). The recovered DNA fragment was digested with EcoRI and HindIII as described above, and subjected to a second round of gel purification as described above using electroelution and subsequent visual quantitation.

c.) Phenol/chloroform extraction: A 600 µl aliquot of the PCR pool was extracted twice using an equal volume of phenol/chloroform (49:1) followed by ethanol precipitation in the presence of sodium acetate. The precipitate was then digested, purified by electrophoresis, ethanol precipitated and visually quantitated as described above.

d.) Anti-Taq Antibody treatment: A 600 µl aliquot of the PCR pool was added to 6 µl of TaqStart antibody (CloneTech). Per the manufacturer's recommendations, this was an appropriate amount of antibody to inactivate 25–30 units of Taq, the amount that was initially present in the amplification reaction mixture. The reaction was incubated at about 20–25° C. for 40 minutes to allow the antibody to bind to the Taq enzyme. Following this incubation, the reaction mix was digested with EcoRI and HindIII in React 2 buffer and then ethanol precipitated as above. The sample was then subjected to agarose gel electrophoresis, electroelution and visual quantitation as described above.

Following these various treatments and visual quantitation of the resulting inserts, the inserts were ligated into the pPROEX-CAT vector. Ligation reactions were set up at a 1:1 (10 ng insert: 100 ng vector) molar ratio, and incubated for 12–18 hours at 12° C. using, T4 DNA ligase in a 20 µl volume. The reactions were then diluted to 100 µl of sterile water, and 5 µl of this dilution were added to 100 µl of transformation-competent DH10B *E. coli* cells (Life Technologies, Inc.). Following transformation, various dilutions of the reaction (1 ml each) were plated out on LBamp and LBcam/IPTG plates (Life Technologies, Inc.) to determine the numbers of recombinant (amp$^r$) and CAT-expressing (cam$^r$) colonies. Results are shown in Table 1.

TABLE 1

Effect of Taq Removal on Cloning Efficiency.

| Post-PCR treatment | Cloning Efficiency Number of Amp$^r$ colonies | Correct Recombinants % Cam$^r$ (No. of Colonies) |
|---|---|---|
| vector-only (neg. control) | 13 | 7 (1) |

TABLE 1-continued

Effect of Taq Removal on Cloning Efficiency.

| Post-PCR treatment | Cloning Efficiency Number of Amp$^r$ colonies | Correct Recombinants % Cam$^r$ (No. of Colonies) |
| --- | --- | --- |
| vector + insert religation (pos. control) | 4250 | 84 (3550) |
| Taq Antibody treatment | 1500 | 85 (1275) |
| Ethanol precipitation | 700 | 22 (154) |
| Gel Purification | 495 | 100 (495) |
| Phenol/chloroform extraction | 2350 | 96 (2256) |

The results shown in Table 1 demonstrate that treatment of the PCR sample with anti-Taq antibody prior to restriction enzyme digestion resulted in a high number of transformants (amp$^r$ colonies), with a large proportion (85%) of these being cam$^r$ indicating that the correct reading frame was maintained during ligation. These results compare favorably with the positive control and also with the phenol/chloroform extraction method, which has been shown previously to result in higher post-PCR cloning efficiencies (Bennett, B. L., and Molenaar, A. J., *BioTechniques* 16(1):36–37 (1994), and which has heretofore been the method of choice for reducing residual Taq activity. Ethanol precipitation of the PCR product followed by digestion and purification resulted in a reduced number of cam$^r$ colonies, consistent with previous reports that ethanol precipitation is insufficient to remove residual Taq DNA polymerase activity (Bennett, B. L., and Molenaar, A. J., *BioTechniques* 16(1):36–37 (1994). Gel purification of the PCR product to remove Taq DNA polymerase prior to RE-digestion resulted in 100% of the amp$^r$ recombinants being cam$^r$, but the overall number of transformants was the lowest compared to the other treatment groups. Furthermore, this double gel purification was the most time-consuming and inefficient method since it resulted in large losses of amplification product due to the manipulations involved in two successive rounds of agarose gel purification.

Together, these data indicate that it is advantageous to use a Taq antibody to facilitate post-PCR cloning of amplified nucleic acid molecules. Such an approach increases the efficiency and yield of clones obtained from amplified nucleic acid molecules, both by decreasing the number of experimental manipulations that are used and by obviating the use of potentially harmful organic solvents (phenol/chloroform) for extraction of residual Taq activity.

Example 2

Radioactive Assay of Efficiency of Cloning of Amplified Nucleic Acid Molecules To confirm the above results in a more sensitive assay, a radioactive method was employed. A 664-bp amplicon, which encodes the 3' end of the chloramphenicol acetyl transferase (CAT) gene, was amplified using Taq DNA polymerase (5 units/100 μl) and the primers detailed in Example 1. For set-up of the radioactive assay, the amplification product (5 μl containing 0.25 units of Taq DNA polymerase at the start of PCR) was incubated in the presence and absence of two different preparations of anti-Taq antibodies ("antibody #1" and "antibody #2"; Life Technologies, Inc. (Rockville, Md.)), for 15 minutes at room temperature (20–25° C.) prior to digestion with EcoRI and HindIII at 37° C. for one hour. Along with the restriction enzymes, 20 uCi of $^{32}$P-dATP was added to each reaction to monitor potential fill-in of 3'-recessed termini by residual Taq DNA polymerase. As an additional positive control, three units of Klenow fragment were added to one reaction to examine maximal incorporation of nucleotides.

Replicate samples were spotted in duplicate onto glass fiber filters followed by precipitation of incorporated nucleotides in the presence of ice cold 10% TCA/0.1% pyrophosphate.

The results of these experiments are shown Table 2.

TABLE 2

Effects of Anti-Taq Antibodies on 3' Terminal Fill-in

| Treatment Before RE Digestion | Incorporation (cpm; replicates) |
| --- | --- |
| TCA precipitation blank (negative control) | 588, 976 |
| none | 7521, 7811, 7182, 6868 |
| RE digestion followed by Klenow treatment (positive control) | 51271, 53619 |
| Antibody #1, 1 unit | 896, 664 |
| Antibody #1, 0.67 units | 598, 660 |
| Antibody #1, 0.33 units | 732, 696 |
| Antibody #2, 1 unit | 600, 602 |
| Antibody #2, 0.67 units | 472, 536 |
| Antibody #2, 0.33 units | 670, 956 |

These results indicate that Taq DNA polymerase does, indeed, catalyze the incorporation of nucleotides into TCA-precipitable material. Both antibody formulations inhibited incorporation of TCA-precipitable counts to approximately background (blank) levels.

To determine if these cpm were incorporated into the clonable fragment, the samples were subjected to agarose-gel electrophoresis followed by autoradiography. As shown in FIG. 1, radiolabel was incorporated into the 522-bp band in samples that were not preincubated with the antibody prior to restriction enzyme digestion. The intensity of this 522-bp band on the x-ray film was greatly diminished in all samples that were incubated with Taq antibody prior to digestion, in support of the data shown above in Table 2.

Together, these results indicate that inclusion of anti-Taq antibodies in the reaction mixture prevents the residual polymerase activity from filling in the 3' recessed termini in restriction enzyme-digested amplified nucleic acid molecules.

Example 3

Cloning of Amplifed Nucleic Acid Molecules

A 664-bp amplicon was amplified using Taq DNA polymerase (5 units/100 μl) as described in Example 1. 50 μl of the amplification reaction (2.5 units of Taq DNA polymerase) were removed and incubated with 3.3 units (10 μl) of anti-Taq antibody (Life Technologies, Inc.; Rockville, Md.) for seven minutes at room temperature (about 20–25° C.). Two additional 50 μl aliquots were incubated with 10 μl of antibody dilution buffer to serve as the control reactions. Following this preincubation, all three reactions were incubated with 60 units each of EcoRI and HindIII in a total volume of 120 μl in React-2 buffer for one hour at 37° C. Five units of Klenow enzyme were added to one of the control reactions and incubated for an additional 10 minutes at 37° C. to examine how filling in the 3' recessed ends of the digested amplicon affects the number of colonies obtained in a cloning experiment. All three reactions mixtures were ethanol precipitated and subjected to agarose gel electrophoresis and the 522-bp clonable DNA was gel purified using GlassMax as described in Example 1. Following purification, the concentration of the three different insert preparations was determined using a Kodak Digital Imaging Camera so that equivalent amounts of the purified 522-bp insert were added to each ligation reaction.

The three inserts were each ligated into gel-purified pPROEXCAT that had been digested with EcoRI and HindIII. One tenth of the ligation was transformed into DH5α subcloning-competent E. coli cells (Life Technologies, Inc.), and the transformations were plated in triplicate onto LB plates containing 100 μg/ml ampicillin and X-gal, and onto LB plates containing 100 μg/ml ampicillin, 7.5 μg/ml chloramphenicol, X-gal and IPTG. The chloramphenicol/IPTG platings were performed to assess the percentage of cam$^r$ recombinants, as an indication of the number of in-frame ligations as described above. Results are shown in Table 3.

TABLE 3

Efficiency of Cloning of Amplified Nucleic Acid Molecules.

| Sample | No. of amp$^r$ colonies | No. of cam$^r$ colonies |
|---|---|---|
| vector-only (neg. control) | 17 | 16 |
| Klenow fill-in (pos. control) | 155 | 31 |
| no antibody | 28 | 48 |
| anti-Taq antibody | 1317 | 932 |
| insert only (neg. control) | 0 | nd* |

*nd = not determined

These results demonstrate that the addition of Taq antibody to the reaction, prior to restriction enzyme-mediated generation of 3' recessed termini, augments the efficiency of cloning of the amplified inserts. Based on these findings, it is therefore desirable to add a polymerase inhibitor, such as an anti-Taq antibody, to the reaction mixture prior to digestion of PCR products with restriction enzymes, in order to increase the efficiency of cloning of the amplified nucleic acid molecules.

Example 4

Simultaneous Treatment of Amplified Nucleic Acid Molecules with Anti-Taq Antibodies and Restriction Enzymes The results shown in Example 3 indicate that sequential addition of polymerase inhibitors and restriction endonucleases greatly increases the efficiency of cloning of amplified nucleic acid molecules. To determine if this sequential addition of these reagents was necessary, the cloning experiments described in Example 3 were repeated, except that the anti-Taq antibody was added to the reaction simultaneously with the EcoRI and HindIII restriction enzymes (i.e., no preincubation, as in Example 3, was performed). In addition, a 1:1 ratio of Taq and anti-Taq antibody (per the unit definition of the antibody noted above) was employed, all other experimental techniques were the same as in Example 3.

Results of these experiments are shown in Table 4.

TABLE 4

Simultaneous Addition of Antibody and Restriction Enzymes.

| Sample Treatment | No. of amp$^r$ colonies | No. of cam$^r$ colonies |
|---|---|---|
| vector-only (neg. control) | 4 | 5 |
| Klenow fill-in (pos. control) | 9 | 7 |
| no antibody | 10 | 8 |
| anti-Taq antibody | 741 | 520 |
| pUC 19 transformation control* | 30 | 0 |

*Transformation/plating control to demonstrate no growth on the chloramphenicol plates with a vector which cannot support CAT expression. Not corrected back to transformation efficiency (cfu/μg).

These results confirm those of Example 3, indicating that treatment of the amplification reaction mixture with a polymerase inhibitor, such as an anti-Taq antibody, increases the efficiency of cloning of the amplified nucleic acid molecules. More importantly, these results indicate that the polymerase inhibitors and the restriction endonucleases may be added to the reaction mixture simultaneously or sequentially, with equivalent results.

Example 5

Reduction of Taq DNA Polymerase-mediated Artifacts by Treatment of PCR Reactions with Anti-Taq Antibodies When T/A cloning is performed, amplified nucleic acid is mixed (without purification) with the cloning vector and then ligation is performed and host cells transformed. The efficiency of this cloning method can be extremely variable. One parameter affecting efficiency is the stability of the vector which has 3' dT overhangs that are needed to get specific annealing with the amplified product. In order to investigate the effect of Taq and other components of the PCR reaction on the vector itself during ligation, the following experiment was done. A mock PCR reaction was prepared that contained all the components of a normal reaction except template and primers. Thirty cycles of amplification were performed, and an aliquot of this PCR reaction which was equivalent to that normally used was added to the vector either with or without anti-Taq antibodies (obtained from Life Technologies, Inc.; Rockville, Md.). The ligation reaction and transformation were then performed according to the manufacturer's instructions (Invitrogen). The screen for transformants in this system was a determination of the lack of LacZα complementation (presence of white colonies) as described in Sambrook, J., et al., *Molecular Cloning, A Laboratory Manual*, 2nd ed., Cold Spring Harbor, N.Y.: Cold Spring Harbor Laboratory (1989). In an ideal situation, there should be no colonies of any kind with the vector alone in the ligation; typically, however, there a very small number of background colonies are observed (i.e., 1–5 white colonies and 2–20 blue colonies). White colonies result when the expression of the LacZα is stopped by insertion of an amplified product, or in this case by some other mechanism (for example, exonuclease contamination that chews back the ends of the vector). Blue colonies are presumed to arise from religation of the vector that has lost the 3' dT overhang and is religated resulting in the expression of the α peptide.

As shown in Table 5, the presence of untreated Taq DNA polymerase (in the PCR reaction mixtures) in the samples containing ligated vector alone resulted in dramatically increased background (white/green colonies). This background was reduced substantially in the samples that were treated with anti-Taq antibody prior to ligation.

TABLE 5

Reduction of Taq-mediated Cloning Artifacts Using Anti-Taq Antibodies

| Sample | No. of White Colonies | No. of Blue Colonies |
|---|---|---|
| Vector + Taq (PCR reaction) | 41, 122 | 30, 13 |
| Vector + Taq (PCR reaction) + antibody | 1, 4 | 2, 42 |
| Vector alone | 1, 0 | 2, 24 |

These results indicate that Taq may have a deleterious effect on the vector (e.g., modifying the 3' and/or 5' termini) and may account for the large variability in efficiency seen with T/A cloning. Reduction of this artifact, for example by use of anti-Taq antibody according to the methods of the present invention, leads to decreased background (lower number of colonies) and reduced variation in cloning efficiency.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of cloning an amplified or synthesized nucleic acid molecule, comprising:
   (a) amplifying or synthesizing one or more nucleic acid molecules in the presence of one or more polypeptides having polymerase activity to produce amplified or synthesized nucleic acid molecules;
   (b) incubating said amplified or synthesized nucleic acid molecules with one or more inhibitors of the polypeptides having polymerase activity under conditions sufficient to inhibit or inactivate the polymerase activity, wherein said one or more inhibitors is an antibody or fragment thereof; and
   (c) inserting said amplified or synthesized nucleic acid molecules into one or more host cells.

2. The method of claim 1, wherein said insertion step (c) further comprises digesting said amplified or synthesized nucleic acid molecules with one or more restriction endonucleases, to produce digested nucleic acid molecules.

3. The method of claim 2, wherein said insertion step (c) further comprises ligating said digested nucleic acid molecules into one or more vectors to form one or more genetic constructs.

4. The method of claim 1, wherein said insertion step (c) further comprises ligating said amplified or synthesized nucleic acid molecules into one or more vectors to form one or more genetic constructs.

5. The method of claim 3 or claim 4, wherein said insertion step (c) further comprises transforming said one or more genetic constructs into one or more host cells.

6. The method of claim 1, wherein said one or more inhibitors prevent or inhibit modification of one or more termini of said amplified or synthesized nucleic acid molecules.

7. The method of claim 2, wherein said one or more inhibitors prevent or inhibit modification of one or more termini of said digested nucleic acid molecules.

8. The method of claim 1, wherein said one or more inhibitors allow increased efficiency of cloning of said amplified or synthesized nucleic acid molecules into one or more vectors.

9. The method of claim 2, wherein said one or more inhibitors allow increased efficiency of cloning of said digested nucleic acid molecules into one or more vectors.

10. The method of claim 1, wherein said amplifying or synthesizing comprises:
    (a) contacting a first nucleic acid molecule, a first primer molecule which is complementary to a portion of said first nucleic acid molecule, a second nucleic acid molecule and a second primer molecule which is complementary to a portion of said second nucleic acid molecule, with one or more polypeptides having polymerase activity;
    (b) incubating said molecules under conditions sufficient to form a third nucleic acid molecule complementary to all or a portion of said first nucleic acid molecule and a fourth nucleic acid molecule complementary to all or a portion of said second nucleic acid molecule;
    (c) denaturing said first and third and said second and fourth nucleic acid molecules; and
    (d) repeating steps (a) through (c) one or more times.

11. The method of claim 1, wherein said one or more polypeptides are selected from the group consisting of DNA polymerases and reverse transcriptases.

12. The method of claim 11, wherein said polypeptides are selected from the group consisting of Taq DNA polymerase, Tne DNA polymerase, Tma DNA polymerase, Pfu DNA polymerase, Tfl DNA polymerase, Tth DNA polymerase, Pwo DNA polymerase, Tli DNA polymerase, Pyrococcus species GB-D DNA polymerase, T7 DNA polymerase, T5 DNA polymerase, DNA polymerase III, Klenow fragment DNA polymerase, Stoffel fragment DNA polymerase, and mutants, fragments or derivatives thereof.

13. The method of claim 11, wherein said polypeptides are selected from the group consisting of M-MLV reverse transcriptase, RSV reverse transcriptase, AMV reverse transcriptase, RAV reverse transcriptase, MAV reverse transcriptase, HIV reverse transcriptase, M-MLV H reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase, and mutants, fragments or derivatives thereof.

14. The method of claim 11, wherein one of said DNA polymerases is Tne DNA polymerase or a mutant, fragment or derivative thereof.

15. The method of claim 11, wherein one of said polypeptides is Tma DNA polymerase or a mutant, fragment or derivative thereof.

16. The method of claim 11, wherein one of said polypeptides is Taq DNA polymerase or a mutant, fragment or derivative thereof.

17. The method of claim 11, wherein one of said polypeptides is a T7 DNA polymerase or a mutant, fragment or derivative thereof.

18. A method of ligating amplified or synthesized nucleic acid molecules into a vector with increased efficiency, comprising:
(a) forming a mixture comprising said amplified or synthesized nucleic acid molecules and one or more polymerase inhibitors, wherein said one or more inhibitors is an antibody or fragment thereof; and
(b) ligating said nucleic acid molecules into one or more vectors to form one or more genetic constructs.

19. The method of claim 18, wherein said mixture further comprises one or more polypeptides having polymerase activity.

20. The method of claim 18, further comprising transforming said one or more genetic constructs into one or more host cells.

21. A method for cloning one or more nucleic acid molecules into one or more vectors, comprising:
(a) forming a mixture comprising said nucleic acid molecules to be cloned, said vectors and one or more polymerase inhibitors, wherein said one or more inhibitors is an antibody or fragment thereof; and
(b) ligating said nucleic acid molecules into said vectors to form one or more genetic constructs, thereby cloning said one or more nucleic acid molecules.

22. The method of claim 21, wherein said mixture further comprises one or more polypeptides having polymerase activity.

23. The method of claim 21, further comprising transforming said one or more genetic constructs into one or more host cells.

24. A method for cloning one or more nucleic acid molecules into one or more vectors, comprising:
(a) forming a mixture comprising said nucleic acid molecules to be cloned, one or more polymerase inhibitors and one or more restriction endonucleases, wherein said one or more inhibitors is an antibody or fragment thereof; and
(b) ligating said nucleic acid molecules into one or more vectors to form one or more genetic constructs, thereby cloning said one or more nucleic acid molecules into one or more vectors.

25. The method of claim 24, wherein said mixture further comprises one or more polypeptides having polymerase activity.

26. The method of claim 24, further comprising transforming said one or more genetic constructs into one or more host cells.

27. The method of any one of claims 1, 8, 21, or 24, wherein said antibody or fragment thereof is selected from the group consisting of an anti-Taq antibody, an anti-Tne antibody, an anti-Tma antibody, an anti-Pfu antibody and fragments thereof.

* * * * *